United States Patent
Peterson et al.

(10) Patent No.: US 11,857,626 B2
(45) Date of Patent: Jan. 2, 2024

(54) METHOD OF ENHANCING MENTAL FUNCTION AND ACUITY BY DELIVERING BIOCHEMICAL SCAFFOLDS

(71) Applicant: Next2Me, LLC, Oakland, CA (US)

(72) Inventors: Ralph L Peterson, Oakland, CA (US); Renee D Williman, Oakland, CA (US)

(73) Assignee: Next2Me, LLC, Oakland, CA (US)

( * ) Notice: Subject to any disclaimer, the term of this patent is extended or adjusted under 35 U.S.C. 154(b) by 65 days.

(21) Appl. No.: 18/111,702

(22) Filed: Feb. 20, 2023

(65) Prior Publication Data

US 2023/0201347 A1 Jun. 29, 2023

Related U.S. Application Data

(63) Continuation-in-part of application No. 17/961,836, filed on Oct. 7, 2022, now Pat. No. 11,612,630, which is a continuation-in-part of application No. 17/732,639, filed on Apr. 29, 2022, now Pat. No. 11,529,383, which is a continuation-in-part of application No. 16/116,539, filed on Aug. 29, 2018, now abandoned, which is a continuation-in-part of application No. 14/223,392, filed on Mar. 24, 2014, now abandoned.

(60) Provisional application No. 61/936,116, filed on Feb. 5, 2014.

(51) Int. Cl.
| | |
|---|---|
| A61K 41/00 | (2020.01) |
| A61K 31/51 | (2006.01) |
| A61K 31/714 | (2006.01) |
| A61K 31/4415 | (2006.01) |
| A61K 36/68 | (2006.01) |
| A61K 36/23 | (2006.01) |
| A61K 36/06 | (2006.01) |
| A61K 31/4188 | (2006.01) |
| A61K 31/525 | (2006.01) |
| A61K 31/455 | (2006.01) |
| A61K 31/197 | (2006.01) |
| A61K 31/661 | (2006.01) |
| A61K 31/519 | (2006.01) |
| A61K 36/9068 | (2006.01) |

(52) U.S. Cl.
CPC ........ *A61K 41/0004* (2013.01); *A61K 31/197* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/661* (2013.01); *A61K 31/714* (2013.01); *A61K 36/06* (2013.01); *A61K 36/23* (2013.01); *A61K 36/68* (2013.01); *A61K 36/9068* (2013.01)

(58) Field of Classification Search
CPC ..... A61K 41/0004; A61K 31/51; A61K 36/06
See application file for complete search history.

(56) References Cited

FOREIGN PATENT DOCUMENTS

| | | | | |
|---|---|---|---|---|
| CA | 2609821 A1 | * | 11/2006 | ........... A61K 9/0056 |
| WO | WO-2011003045 A1 | * | 1/2011 | ........... A61K 31/191 |

OTHER PUBLICATIONS

Pershin, S.M. Harmonic Oscillations of the Concentration of H-Bonds in Liquid Water; Laser Spectroscopy, vol. 16, No. 8, pp. 1184-1190. (Year: 2006).*

* cited by examiner

*Primary Examiner* — Sharmila G Landau
*Assistant Examiner* — Paul C Martin
(74) *Attorney, Agent, or Firm* — Francis Law Group

(57) ABSTRACT

Biochemical scaffolds for regulating mammalian cell function. The biochemical scaffolds include a base liquid medium, a bioenergetic platform and a vibrational platform. The bioenergetic platform includes at least one Krebs cycle modulator and/or neurotransmitter modulator. The vibrational platform includes at least one energy signature component, e.g., an herb. The biochemical scaffold is subjected to harmonic oscillation for a defined, predetermined period of time, wherein the energy signature of the energy signature component is imparted to, captured, replicated, and retained by the liquid medium, and, when the biochemical scaffolds are delivered to and, thus, in communication with biological tissue, the biochemical scaffolds induce specific biochemical activities via the resonant transfer of the retained energy signature to the biological tissue and, hence, endogenous cells thereof.

10 Claims, 5 Drawing Sheets

--Prior Art--

--Prior Art--

N2M BIOCHEMICAL SCAFFOLDS

| Modulator | Physiological Action/Reaction | Element/Compound |
|---|---|---|
| Krebs Cycle Modulator | 1) Induce and/or modulate at least one Krebs cycle metabolic reaction, process and/or pathway<br><br>2) Induce production of $CO_2$, acetyl-CoA, $FADH_2$ and adenosine triphosphate (ATP) | ashwaganda, eleuthero root (or extract), maca, an amino acid, e.g., L-arginine and L-citrulline, and vitamins $B_2, B_1, B_3, B_5,$ and $B_9$ |
| Glutathione Modulator | 1) Induce the generation and/or proliferation of glutathione and/or a member of the glutathione family and, thereby, conversion of hydrogen peroxide to $H_2O$ and $O_2$<br><br>2) Induce the synthesis of catalase, i.e. an antioxidant | schisandra chinensis berry, damiana and epimedium and vitamine $B_2$<br><br>maca, nettles leaves, Fe and Cu, and vitamins $B_2, B_5, B_6$ and $B_7$ |
| Neurotransmitter Modulator | Induce the generation of electrochemical signals, i.e., neurotransmitters, and/or modulate the transmission thereof by and between neurons and, hence, cells | cannabidiol (DBD), epimedium, nettle leaf, maca, eleuthero root, Yohimbe, and vitamins $B_1$ and $B_6$ |

*FIG. 4A*

N2M BIOCHEMICAL SCAFFOLDS

| Modulator | Physiological Action/Reaction | Element/Compound |
|---|---|---|
| DNA Modulator | Support and/or enhance mitochondrial DNA activity | vitamin $B_{12}$ |
| Endocannabinoid System Modulator | Induce cell receptor activity; particularly, cannabinoid receptor activity | cannabidiol (CBD) |

*FIG. 4B*

METHOD OF ENHANCING MENTAL FUNCTION AND ACUITY BY DELIVERING BIOCHEMICAL SCAFFOLDS

CROSS-REFERENCES TO RELATED APPLICATIONS

This application is a continuation-in-part of U.S. application Ser. No. 17/961,836, filed Oct. 7, 2022, now U.S. Pat. No. 11,612,630, which is a continuation-in-part of U.S. application Ser. No. 17/732,639, filed Apr. 29, 2022, now U.S. Pat. No. 11,529,383, which is a continuation-in-part of U.S. application Ser. No. 16/116,539, filed Aug. 29, 2018, now abandoned, which is a continuation-in-part of U.S. application Ser. No. 14/223,392, now abandoned, filed on Mar. 24, 2014, which claims the benefit of U.S. Provisional Application No. 61/936,116, filed on Feb. 5, 2014.

FIELD OF THE INVENTION

The present invention relates to compositions and methods for inducing cell activity. More particularly, the present invention relates to biochemical scaffolds and associated methods for inducing, supporting and/or enhancing cell activity and, thereby, function.

BACKGROUND OF THE INVENTION

As is well known in the art, optimal cell activity and, hence, function is essential to human existence. Cell activity and function is primarily dependent on the energy potential of a cell. Where cellular energy has been reduced, a cascade of undesirable cellular events can, and often will, result. The noted cellular events typically result in one or more undesirable physiological characteristics, such as reduced stamina or endurance, and mental clarity.

Reduction of cellular energy can also result in dysfunction of various organs, e.g., heart and/or liver failure. When cellular energy approaches zero, cell death, i.e., apoptosis, is often encountered.

As is also well known in the art, cellular energy is directly dependent on various biochemical processes; particularly, cell respiration, i.e., metabolic reactions and processes that take place in the cells to convert biochemical energy from nutrients into adenosine triphosphate (ATP).

The metabolic reactions and processes, which are often referred to as a metabolic pathway, are typically embodied in the Krebs cycle.

Referring to FIG. 1, there is shown a schematic illustration of a Krebs cycle. As illustrated in FIG. 1, through catabolism of carbohydrates, fats, and proteins, a two carbon organic product, i.e., acetate in the form of acetyl-CoA, is produced. Acetyl-CoA and two equivalents of water ($H_2O$) are consumed during the citric acid cycle, producing two equivalents of carbon dioxide ($CO_2$) and one equivalent of HS-CoA.

In addition, one complete evolution of the Krebs cycle converts three equivalents of nicotinamide adenine dinucleotide ($NAD^+$) into three equivalents of reduced $NAD^+$ (NADH), one equivalent of ubiquinone (Q) into one equivalent of reduced ubiquinone ($QH_2$), and one equivalent each of guanosine diphosphate (GDP) and inorganic phosphate ($P_i$) into one equivalent of guanosine triphosphate (GTP). The NADH and $QH_2$ generated during the Krebs cycle are in turn used by the oxidative phosphorylation pathway to generate adenosine triphosphate (ATP).

A primary source of acetyl-CoA is carbohydrates, which are broken down by glycolysis to produce pyruvate. Pyruvate, in turn, is decarboxylated by the enzyme pyruvate dehydrogenase. The decarboxylated pyruvate generates acetyl-CoA, according to the following equation:

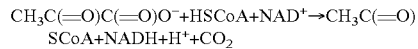

where;

$CH_3C(=O)C(=O)O^-$ represents pyruvate; and
$CH_3C(=O)SCoA$ represents acetyl-CoA.

Regulation of the Krebs cycle is largely dependent upon product inhibition and substrate availability. For example, NADH, a product of all dehydrogenases in the cycle (with the exception of succinate dehydrogenase) inhibits pyruvate dehydrogenase, isocitrate dehydrogenase, α-ketoglutarate dehydrogenase, and citrate synthase. Acetyl-CoA inhibits pyruvate dehydrogenase, while succinyl-CoA inhibits alpha-ketoglutarate dehydrogenase and citrate synthase.

Various elements and compositions have thus been employed to modulate one or more Krebs cycle processes to enhance cell activity and, thereby, generation of ATP. For example, calcium has been successfully employed to regulate the Krebs cycle. Calcium activates pyruvate dehydrogenase phosphatase, which, in turn, activates the pyruvate dehydrogenase complex. Calcium also activates isocitrate dehydrogenase and α-ketoglutarate dehydrogenase. This increases the reaction rate of many of the sequences in the cycle, and therefore increases flux throughout the pathway.

Citrate has also been employed as a feedback inhibitor. Citrate inhibits phosphofructokinase, i.e., an enzyme involved in glycolysis that catalyzes formation of fructose 1,6-bisphosphate, which is a precursor of pyruvate. This inhibits the formation of a high rate of flux when there is an accumulation of citrate.

Recent efforts have also been directed to the link between intermediates of the Krebs cycle and the regulation of hypoxia-inducible factors (HIFs). HIFs play a role in the regulation of oxygen homeostasis, and are transcription factors that target angiogenesis, vascular remodeling, glucose utilization, iron transport, and apoptosis.

HIFs are synthesized constitutively. Hydroxylation of at least one of two critical proline residues also mediates their interaction with the von Hippel Lindau E3 ubiquitin ligase complex, which targets them for rapid degradation. This reaction is catalyzed by prolyl 4-hydroxylases.

Various elements and compositions, such as fumarate and succinate, have thus been employed to inhibit the formation of prolyl hydroxylases and, thereby, stabilize seminal HIFs.

Although some of the noted elements and compositions have garnered some success in inducing Krebs cycle activity and, thereby cell activity and function (and, hence, enhancing ATP energy), there remains a need for improved biochemical formulations that effectively and readily enhance cell activity by inducing and/or modulating multiple Krebs cycle reactions and/or pathways.

Various formulations and efforts have also been employed to enhance cell activity and function and, thereby, physical and mental function, by inducing or modulating other molecular actions, including inducing the generation and transmission of electrochemical signals, i.e., neurotransmitters, inducing DNA activity and inducing and/or modulating cell receptor activity.

Although the noted efforts have similarly garnered some success in enhancing cell activity and function, and, thereby, physical and mental function, there still remains a need for biochemical scaffolds that more effectively enhance physical and mental function.

It would thus be desirable to provide improved biochemical scaffolds, i.e., formulations, and methods associated therewith that enhance physical and mental function by inducing and/or modulating a plurality of seminal molecular and cell activities.

It is therefore an object of the present invention to provide biochemical scaffolds and methods associated therewith that enhance physical and mental function by inducing and/or modulating a plurality of seminal molecular and cell activities.

It is thus one object of the present invention to provide biochemical scaffolds and methods associated therewith that enhance mental function and acuity by inducing and/or modulating at least one Krebs cycle metabolic reaction, process, and/or pathway.

It is another object of the present invention to provide biochemical scaffolds and methods associated therewith that enhance mental function and acuity by inducing and/or modulating generation of neurotransmitters and/or modulating the transmission of neurotransmitters by and between neurons.

It is another object of the present invention to provide biochemical scaffolds and methods associated therewith that enhance mental function and acuity by inducing and/or modulating cell receptor activity.

It is another object of the present invention to provide biochemical scaffolds and methods associated therewith that enhance mental function and acuity by inducing and/or modulating mitochondrial DNA activity.

It is another object of the present invention to provide biochemical scaffolds and methods associated therewith that enhance mental function and acuity by inducing and/or modulating endocannabinoid system activity.

SUMMARY OF THE INVENTION

The present invention is directed to biochemical scaffolds and associated methods that enhance mental function and acuity by inducing and/or modulating a plurality of molecular and cell activities.

In some embodiments of the invention, there are thus provided methods for enhancing mental function and acuity of a subject comprising:
(a) providing a biochemical scaffold comprising (i) a liquid medium, (ii) at least one Krebs cycle modulator that is adapted to induce and/or modulate at least one Krebs cycle metabolic reaction, process, and/or pathway, (iii) at least one neurotransmitter modulator adapted to induce and/or modulate generation of neurotransmitters and modulating the transmission thereof by and between neurons, (iv) at least one glutathione modulator adapted to induce catalase synthesis, (v) at least one DNA modulator adapted to induce and/or modulate mitochondrial DNA activity, and (vi) at least one endocannabinoid system modulator adapted to induce and/or modulate endocannabinoid system activity;
(ii) subjecting the biochemical scaffold to harmonic oscillation; and
(iii) delivering a therapeutically effective amount of the biochemical scaffold to the subject.

In a preferred embodiment of the invention, the liquid medium comprises glycerin-based water.

In a preferred embodiment of the invention, the biochemical scaffold comprises a plurality of Krebs cycle modulators comprising vitamin $B_1$, vitamin $B_2$, vitamin $B_3$, vitamin $B_5$ and vitamin $B_9$.

In a preferred embodiment of the invention, the biochemical scaffold comprises a plurality of neurotransmitter modulators comprising ginger root, lion's mane mushroom (*hericium erinaceus*), waterhyssop (*bacopa monnieri*), gotu kola (*centella asiatica*), huperzine A, vitamin E, phosphatidylserine, and vitamin $B_6$.

In a preferred embodiment, the glutathione modulator comprises vitamin $B_7$.

In a preferred embodiment, the DNA modulator comprises vitamin $B_{12}$.

In a preferred embodiment, the endocannabinoid system modulator comprises cannabidiol (CBD).

In some embodiments, the harmonic oscillation comprises a frequency in the range of approximately 0.02 kHz to 10.5 kHz for a period of time in the range of at least 3.0 minutes to 60.0 minutes.

In some embodiments, the harmonic oscillation comprises sequential harmonic oscillation comprising a first frequency in the range of 0.9 kHz to 1.5 kHz for a first period of time in the range of 3.0 minutes to 60.0 minutes, and a second frequency in the range of 9.5 kHz to 10.5 kHz for a second period of time in the range of 3.0 minutes to 60.0 minutes.

In some embodiments, the harmonic oscillation comprises sequential harmonic oscillation comprising a first frequency in the range of 0.9 kHz to 1.5 kHz for a first period of time in the range of 3.0 minutes to 60.0 minutes, a second frequency in the range of 9.5 kHz to 10.5 kHz for a second period of time in the range of 3.0 minutes to 60.0 minutes, a third frequency in the range of 9.5 kHz to 11.0 kHz for a third period of time in the range of 3.0 minutes to 60.0 minutes, a fourth frequency in the range of 0.01 kHz to 0.03 kHz for a fourth period of time in the range of 3.0 minutes to 60.0 minutes, and a fifth frequency in the range of 0.004 kHz to 0.010 kHz for a fifth period of time in the range of 3.0 minutes to 60.0 minutes.

In a preferred embodiment, when the biochemical scaffold is subjected to harmonic oscillation, retained energy signatures of one or more of the above referenced biochemical scaffold formulation components are transferred to the liquid medium, wherein, when the biochemical scaffold is delivered to biological tissue, the biochemical scaffolds further enhance the molecular and cellular activities induced by the Krebs cycle modulators, neurotransmitter modulators, glutathione modulator, DNA modulator and endocannabinoid system modulator through the resonant transfer of the retained energy signatures to the biological tissue and, hence, endogenous cells thereof.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 4A and 4B are tables of biochemical scaffolds, according to the invention.

DETAILED DESCRIPTION OF THE PREFERRED EMBODIMENT

Figure 1:
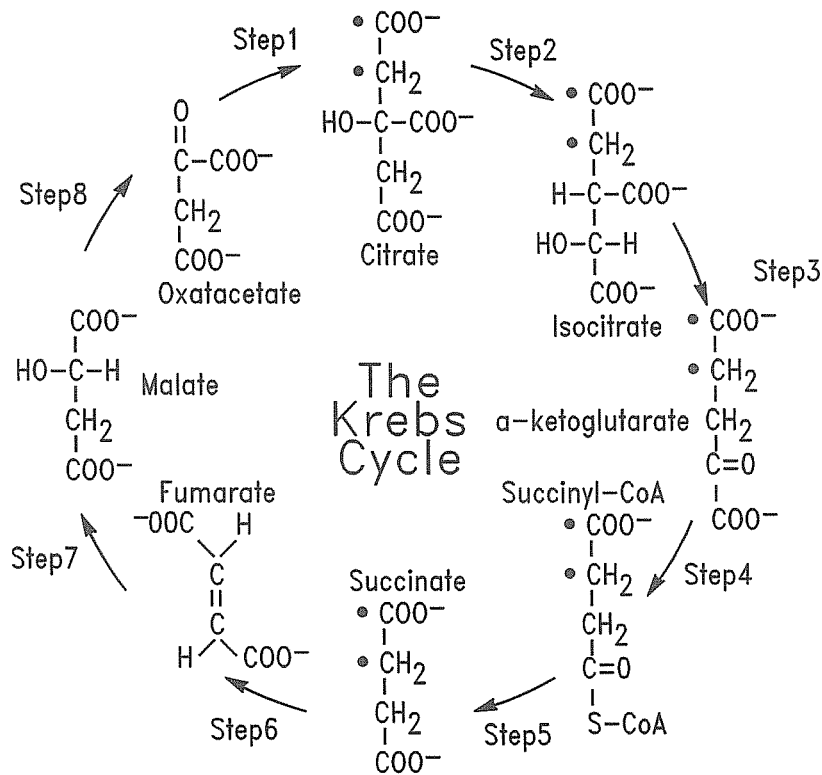
FIG. 1 is a schematic illustration of a Krebs cycle.
Figure 2:
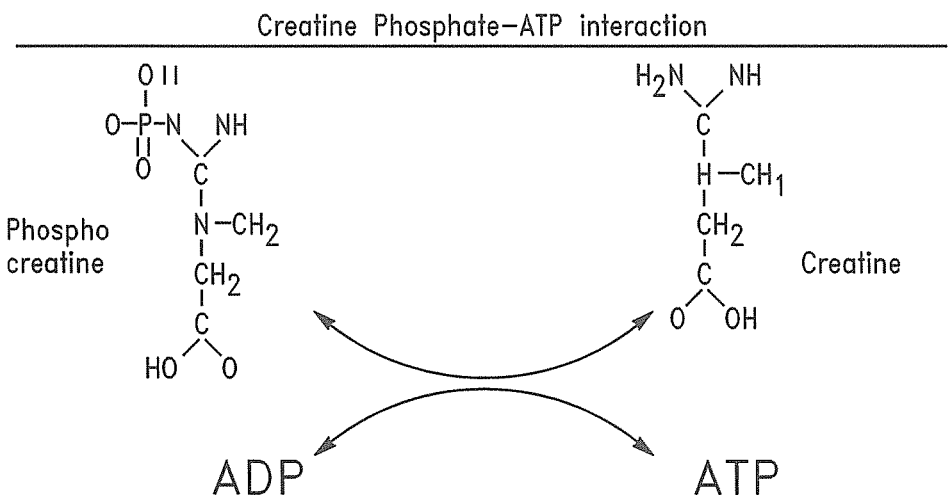
FIG. 2 is a schematic illustration of creatine phosphate—ATP interaction.

Before describing the present invention in detail, it is to be understood that this invention is not limited to particularly exemplified formulations or methods as such may, of course, vary. Thus, although a number of formulations and methods similar or equivalent to those described herein can be used in the practice of the present invention, the preferred formulations and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a", "an" and "the" include plural referents unless the content clearly dictates otherwise.

Definitions

The terms "glycerin" and "glycerin-based water" are used interchangeably herein, and mean and include a solution comprising water (i.e., $H_2O$) and glycerol.

The term "structured water," as used herein, means and includes $H_2O$ comprising a hydrogen bond angle greater than 110°, more preferably, a hydrogen bond angle in the range of approximately 113° to 115°. According to the invention, the term "structured water" also means and includes $H_2O$ that is processed according to at least one of the methods disclosed in U.S. application Ser. No. 16/559,986, which is incorporated by reference herein.

The term "vibrational energy platform," as used herein, means and includes biologically targeted complex, stable, and efficient energetic blanks and glycerol water-soluble molecules, which, when programmed with a laser charged imprint of herbs, minerals, vitamins, amino acids, or pharmaceutical properties (creating energy-signature templates), help stimulate/enable/enhance vital cellular biochemical processes necessary to maintain homeostasis.

The term "biochemical agent" as used herein, means and includes any element, agent, drug, compound, composition of matter or mixture thereof comprising an energy signature component.

The terms "energy signature" and "energy signature component," are used interchangeably herein, mean and include the specific energetic or electromagnetic identity of a selective herb or biochemical agent and, hence, molecular structure(s) thereof when the herb or biochemical agent is exposed to radiation energy, such as radiation energy generated via harmonic oscillation. The terms "energy signature" and "energy signature component," as used interchangeably herein, also mean and include the properties and functions of an herb or biochemical agent associated with the energetic identity of the herb or biochemical agent.

The term "Krebs cycle modulator," as used herein, means and includes an element, agent, drug, compound, composition of matter or mixture thereof, including its formulation, which induces and/or modulates a Krebs cycle metabolic reaction, process and/or pathway, including, without limitation, Krebs cycle product inhibition and/or substrate availability. According to the invention, suitable Krebs cycle modulators can comprise, without limitation, eleuthero root (or extract), maca, an amino acid, e.g., L-arginine and L-citrulline, and vitamins $B_1$, $B_2$, $B_3$, $B_5$, and $B_9$.

The term "neurotransmitter modulator," as used herein, means and includes an element, agent, drug, compound, composition of matter or mixture thereof, including its formulation, which induces the generation or proliferation of at least one neurotransmitter and/or modulates the transmission thereof by and between neurons and, hence, cells.

According to the invention, suitable neurotransmitter modulators comprise, without limitation, epimedium, stinging nettle leaf (also referred to herein as "stinging nettle"), maca root, eleuthero root, ginger root, Yohimbe, vitamin $B_1$, vitamin $B_6$, lion's mane mushroom (*hericium erinaceus*), waterhyssop (*bacopa monnieri*), gotu kola (*centella asiatica*), huperzine A, vitamin E and phosphatidylserine.

The term "glutathione modulator," as used herein, means and includes an element, agent, drug, compound, composition of matter or mixture thereof, including its formulation, which induces the generation or proliferation of glutathione and/or the glutathione family, including, without limitation, glutathione peroxidase.

The term "glutathione modulator" also means and includes an element, agent, drug, compound, composition of matter or mixture thereof, including its formulation, which induces catalase synthesis.

According to the invention, suitable glutathione modulators comprise, without limitation, herbs, including, without limitation, *schisandra chinensis* berry, damiana, epimedium, maca, and stinging nettle leaf; metal ions including iron (Fe) and copper (Cu); and B-vitamins selected from the group comprising vitamins $B_2$, $B_5$, $B_6$, and $B_7$.

The term "DNA modulator," as used herein, means and includes an element, agent, drug, compound, composition of matter or mixture thereof, including its formulation, that induces and/or modulates mitochondrial DNA, including protecting and/or facilitating the repair of mitochondrial DNA. According to the invention, a suitable DNA modulator comprises, without limitation, vitamin $B_{12}$.

The term "endocannabinoid system modulator," as used herein, means and includes an element, agent, drug, compound, composition of matter or mixture thereof, including its formulation, which induces and/or modulates cell receptor activity; particularly, cannabinoid receptor activity, i.e., the activity of CB1 or CB2. According to the invention, a suitable endocannabinoid system modulator comprises, without limitation, cannabidiol (CBD).

The term "nuclear hormone receptor modulator," as used herein, means and includes an element, agent, drug, compound, composition of matter or mixture thereof, including its formulation, which induces and/or modulates cell receptor activity; particularly, nuclear hormone receptor activity, e.g., the activity of estrogen receptor-α (ERα), estrogen receptor-β (ERβ), androgen receptor (AR), and mineralocorticoid receptor (MR). According to the invention, a suitable nuclear hormone receptor modulator comprises, without limitation, red Korean *ginseng*.

The terms "cellular dysfunction" and "cell dysfunction" are used interchangeably herein and mean and include a reduction or impairment in physical structure or function of a cell.

The term "organ dysfunction", as used herein, means and includes a reduction or impairment in physical structure or function of a mammalian organ, including, without limitation, the cardiovascular vascular system (heart and lungs), digestive system (salivary glands, esophagus, stomach, liver, gallbladder, pancreas, intestines, colon, rectum, and anus), endocrine system (hypothalamus, pituitary gland, pineal body, thyroid, parathyroids, and adrenals), excretory system (kidneys, ureters, bladder, and urethra), immune system (lymphatic system, tonsils, adenoids, thymus, and spleen), integumentary system (skin, hair and nails), muscular system, nervous system (brain and spinal cord), reproductive system (ovaries, fallopian tubes, uterus, vagina, mammary glands, prostate, and penis), respiratory system (pharynx, larynx, trachea, bronchi, and diaphragm) and the skeletal system (bones, cartilage, ligaments, and tendons).

The terms "prevent" and "preventing" are used interchangeably herein, and mean and include reducing the frequency or severity of a disease, condition, dysfunction or disorder. The term does not require an absolute preclusion of the disease, condition, dysfunction, or disorder. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition, dysfunction or disorder. The terms include "active treatment", i.e., treatment directed specifically toward the improvement of a disease, pathological condition, dysfunction, or disorder, and "causal treatment", i.e., treatment directed toward removal of the cause of the associated disease, pathological condition, dysfunction, or disorder.

The terms "treat" and "treatment" further include "palliative treatment", i.e., treatment designed for the relief of symptoms rather than the curing of the disease, pathological condition, dysfunction, or disorder, "preventative treatment", i.e., treatment directed to minimizing or partially or completely inhibiting the development of the associated disease, pathological condition, dysfunction, or disorder, and "supportive treatment", i.e., treatment employed to supplement another specific therapy directed toward the improvement of the associated disease, pathological condition, dysfunction, or disorder.

The terms "pharmacological agent," "active agent" and "drug" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans, and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent," "active agent" and "drug" thus mean and include, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, and vasodilating agents.

The term "therapeutically effective", as used herein, means that the amount of a Krebs cycle modulator, glutathione modulator, neurotransmitter modulator, endocannabinoid system modulator, nuclear hormone receptor modulator or DNA modulator and/or biochemical scaffold formed therefrom, or pharmacological or bioactive agent administered to a subject is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "delivery" and "administration" are used interchangeably herein, and mean and include providing a Krebs cycle modulator, glutathione modulator, neurotransmitter modulator, endocannabinoid system modulator, nuclear hormone receptor modulator or DNA modulator and/or biochemical scaffold formed therefrom to a subject through any method appropriate to deliver formulations and/or scaffolds to a subject. Non-limiting examples of delivery methods include oral, sublingual, nasal, direct injection, topical application, etc.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As indicated above, the present invention is directed to biochemical scaffolds and associated methods that induce and/or modulate at least one, more preferably, a plurality of molecular and cellular activities, including, without limitation, (i) at least one Krebs cycle metabolic reaction, process and/or pathway, (ii) generation or proliferation of glutathione and/or a member of the glutathione family and, thereby, induced catalase synthesis, (iii) generation or proliferation of at least one neurotransmitter, and/or modulating the transmission of a neurotransmitter by and between neurons, (iv) mitochondrial DNA activity, and (v) cell receptor activity.

In a preferred embodiment of the invention, the biochemical scaffolds comprise two platforms (and components associated therewith): a vibrational energy platform and a bioenergetic platform.

In some embodiments of the invention, the bioenergetic platforms further comprise a liquid medium. According to the invention, the biochemical scaffold can comprise any suitable medium, such as glycerol water solution (also referred to herein as "glycerin-based water") and distilled water. In some embodiments, the liquid medium comprises oxygen enriched glycerin infused water molecules.

In some embodiments of the invention, the liquid medium comprises structured water. As indicated above, structured water comprises $H_2O$ comprising a hydrogen bond angle greater than 110°, more preferably, a hydrogen bond angle in the range of approximately 113° to 115°.

In some embodiments, the liquid medium comprises glycerin-based water and structured water.

According to the invention, structured water enhances the molecular activities induced by the biochemical scaffolds of the invention; particularly, molecular activities that modulate Krebs cycle metabolic reactions, processes and/or pathways.

As set forth in priority U.S. application Ser. No. 14/223,392, in some embodiments, the biochemical scaffold comprises a glycerol water solution comprising at least 1200 mg/oz. of glycerin.

In some embodiments of the invention, the bioenergetic platforms comprise at least one of the following modulators: a Krebs cycle modulator, glutathione modulator, neurotransmitter modulator, DNA modulator, endocannabinoid modulator or nuclear hormone receptor modulator.

Thus, in some embodiments, the bioenergetic platforms comprise a Krebs cycle modulator and/or glutathione modulator and/or neurotransmitter modulator and/or DNA modulator and/or endocannabinoid modulator and/or nuclear hormone receptor modulator.

In some embodiments, the bioenergetic platforms comprise a plurality of Krebs cycle modulators, and/or glutathione modulators, and/or neurotransmitter modulators, and/or DNA modulators, and/or endocannabinoid modulators and/or nuclear hormone receptor modulators.

As discussed in detail herein, according to the invention, the Krebs cycle modulators induce and/or modulate a Krebs cycle metabolic reaction, process and/or pathway, including, without limitation, Krebs cycle product inhibition and/or substrate availability.

As set forth in FIG. 4A and discussed in detail below, in some embodiments, the Krebs cycle modulators also induce multiple Krebs cycle reactions and/or pathways, resulting in the production of $CO_2$, and/or acetyl-CoA, and/or $FADH_2$, and enhanced adenosine-5'-triphosphate (ATP) energy potential.

As set forth in Applicant's priority U.S. application Ser. Nos. 14/223,392, 16/116,539, 17/732,639, and 17/961,836, ATP is a multifunctional nucleoside triphosphate that is used as a coenzyme in cells. ATP is one of the end products of photophosphorylation and cellular respiration, and is used by structural proteins in many cellular processes, including biosynthetic reactions, motility, and cell division.

Mammalian mitochondria are organelles that produce more than 90% of cellular ATP. In addition to supplying ATP, i.e., cellular energy, mitochondria are also involved in other cellular mechanisms, including cellular differentiation, apoptosis, as well as cell cycle modulation and cell growth.

Mitochondria provide intracellular ATP via a process called glycolysis, which breaks down monosaccharides into ATP through a series of biochemical processes. Mitochondria contain, among other things, the Krebs cycle enzymes that are involved in heme biosynthesis and the electron transport chain, i.e., the Oxidative Phosphorylation pathway (OxPHOS) system. Due to the large flux of redox reactions necessary to maintain oxidative phosphorylation, mitochondria are the primary site of production of reactive oxygen species (ROS).

It has, however, been found that increased production of ROS and interference with the OxPhos system can cause cell cycle dysfunction and arrest.

The OxPHOS system is composed of five large multiprotein enzyme complexes, which collectively transform the reducing energy of NADH and $FADH_2$ to ATP. NADH ubiquinone oxidoreductase (Complex I) contains 45 different subunits, and succinate ubiquinone reductase (Complex II), ubiquinone-cytochrome c oxidoreductase (Complex III), cytochrome c oxidase (Complex IV), and the ATP synthase (Complex V) contain 4, 11, 13 and 16 subunits, respectively.

Four of the OxPHOS enzyme complexes (Complexes I, III, IV and V) have a dual genetic origin, i.e., they are composed of both nuclear DNA-encoded proteins and mitochondrial DNA-encoded proteins.

Transient ischemia (anoxia) results in the local production of extremely high levels of reactive oxygen species (ROS), which can cause long term damage to mitochondria. In the initial phase of transient ischemia, oxygen is scarce, but tissue demands for ATP remain high, resulting in continued functioning of the OxPhos system except for the terminal reduction of oxygen to water by Complex IV. Therefore, reduced electron acceptors "upstream" of Complex IV accumulate to abnormally high levels.

Upon resupply of oxygen, these excess reduced carriers react directly with oxygen to generate highly toxic partially reduced ROS, which are capable of protein, lipid, and DNA modifying reactions. The resulting oxidative damage is deemed to occur mainly inside the mitochondrion, because such ROS are so reactive that they are short lived and cannot diffuse far before finding a target for reaction.

Accordingly, OxPHOS proteins and DNA are deemed the cellular molecules most affected by such oxidative stress. The resulting defects in DNA and OxPHOS proteins can, and in most instances will, result in continued increased production of ROS.

However, it has been found that modulating the OxPhos system and, thereby, ROS production, which can be achieved by the Krebs cycle modulators of the invention, oxidative stress of cells can be substantially reduced or eliminated.

In a preferred embodiment of the invention, the Krebs cycle modulators of the invention comprise, without limitation, *schisandra chinensis* berry, epimedium, stinging nettle, yohimbe, red Korean *ginseng*, eleuthero root (or extract), damiana, ashwagandha, maca, L-arginine and L-citrulline, and vitamins $B_1$, $B_2$, $B_3$, $B_5$, $B_7$, $B_9$, and $B_{12}$.

As discussed in detail herein, in a preferred embodiment of the invention, the glutathione modulators of the invention induce the generation or proliferation of glutathione and/or a member of the glutathione family, including, without limitation, glutathione peroxidase, and/or catalase synthesis.

In a preferred embodiment, the glutathione modulators of the invention comprise, without limitation, *schisandra chinensis* berry, epimedium, stinging nettle, yohimbe, red Korean *ginseng*, eleuthero root (or extract), damiana, ashwagandha, maca, iron (Fe), copper (Cu), and vitamins $B_1$, $B_2$, $B_3$, $B_5$, $B_7$, $B_9$, and $B_{12}$.

As discussed in detail herein, in a preferred embodiment of the invention, the neurotransmitter modulators of the invention induce and/or modulate the generation of neurotransmitters and modulate the transmission thereof by and between neurons and, hence, cells.

In a preferred embodiment, the neurotransmitter modulators of the invention comprise, without limitation, epimedium, stinging nettle, maca, eleuthero root, yohimbe, lion's mane mushroom (*hericium erinaceus*), waterhyssop (*bacopa monnieri*), gotu kola (*centella asiatica*), huperzine A, vitamin $B_1$, vitamin $B_6$, vitamin E and phosphatidylserine.

As also discussed in detail herein, in a preferred embodiment, the DNA modulators support and/or enhance mitochondrial DNA activity by protecting and/or facilitating the repair of mitochondrial DNA.

In a preferred embodiment of the invention, the DNA modulators comprise, without limitation, vitamin $B_{12}$.

In a preferred embodiment of the invention, the endocannabinoid system modulators induce cell receptor and endocannabinoid system activity.

In a preferred embodiment, the endocannabinoid system modulators comprise, without limitation, cannabidiol (CBD) or a component thereof.

In some embodiments of the invention, the bioenergetic platforms further comprise a nuclear hormone receptor modulator.

In a preferred embodiment of the invention, the nuclear hormone receptor modulators induce cell receptor activity; preferably, nuclear hormone receptor modulator activity, e.g., the activity of nuclear hormone receptor modulators estrogen receptor-α (ERα), estrogen receptor-β (ERβ), androgen receptor (AR), and mineralocorticoid receptor (MR).

In a preferred embodiment of the invention, the nuclear hormone receptor modulator comprises red Korean *ginseng*.

Vibrational Energy Platform

As discussed in detail below, in a preferred embodiment of the invention, the vibrational energy platforms of the invention comprise at least one energy signature component derived from at least one biochemical scaffold formulation component, i.e., an herb or biochemical agent.

It has been found and Applicant has confirmed that specific, critical frequencies of radiation energy create an interaction by and between a selective herb or biochemical agent and a suitable medium; more particularly, by and between the herb or biochemical agent and electric dipole structures of water molecules in a glycerin-based water, i.e., a glycerol water solution, whereby permanent polarization of the glycerol water molecules, i.e., coherent glycerol water molecules, is generated.

It has also been found and Applicant has also confirmed that water molecules behave as an "active" medium that can capture, replicate, and retain energy signatures of an herb or biochemical agent through defined harmonic oscillation frequencies. Indeed, Applicant has confirmed that highly specific short-range hydrogen bond and electric dipole-to-dipole static interactions between water molecules can be modulated by defined harmonic oscillation frequencies to generate quantum coherent water molecules (also referred to as "energetic blanks"), which form self-assembled coherence domains (CDs) that capture, replicate, and retain energy signatures of herbs and biochemical agents in energy blank regions of the coherence domains.

Figure 5:
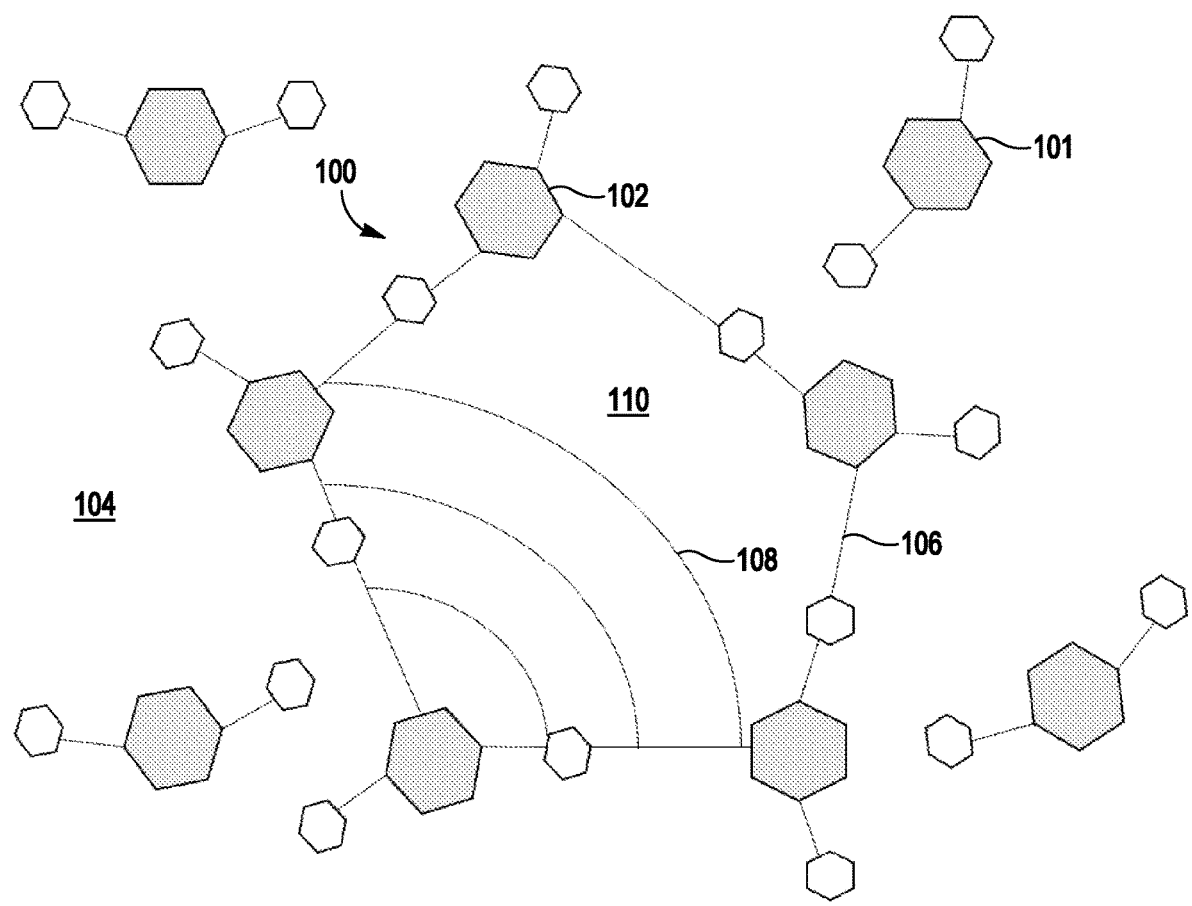
FIG. 5 is a schematic illustration of a coherent domain in a glycerol water solution.

Referring now to FIG. 5, there is shown a coherence domain 100 in a glycerol water solution 104 that comprises a series of quantum coherent water molecules 102, which are bound via short-range hydrogen bonds 106. As illustrated in FIG. 5, the coherence domain 100 comprises an energy signature 108 of a selective herb or biochemical agent that is retained within the energy blank region 110. The coherence domain 100 preferably oscillates in unison with the energy signature 108 retained within the energy blank region 110.

According to the invention, when at least one herb and/or biochemical agent of the invention and a glycerol water solution 104 are subjected to harmonic oscillation at a defined frequency range or sequential harmonic oscillation at defined frequency ranges for a defined, predetermined period of time, the water molecules 101 in the glycerol water solution 104 exhibit quantum coherence, whereby a plurality of distinct quantum coherent water molecules 102 and, hence, coherent domains 100, are generated in the glycerol water solution 104, and, thereby, a unique glycerol water solution (i.e., vibrational energy platform) comprising the following two separate and distinct forms of water molecules is formed: (i) complex, stable quantum coherent water molecules 102, i.e., "energetic blanks," and (ii) water molecules 101.

The quantum coherent water molecules 102 of the glycerol water solution 104, i.e., distinct energetic blanks, form coherent domains 100 that capture, replicate, and retain defined energy signatures 108 of the selective herb and/or biochemical agent of the invention and, hence, chemical components thereof in the energy blank region 110 of the coherence domains 100, i.e., the energy signature 108 of the selective herb and/or biochemical agent is imparted to, captured, replicated, and retained by the coherent domains 100 formed by the quantum coherent water molecules 102 of the glycerol water solution 104.

Applicant has found that when a glycerol water solution comprising coherent domains with a retained energy signature of a selective herb or biochemical agent, i.e., a biochemical scaffold, is delivered to and, hence, is in communication with biological tissue, the biochemical scaffold induces specific biochemical activities through the resonant transfer of the retained energy signatures to the biological tissue and, hence, endogenous cells thereof, whereby a mechanism for the precise regulation of biochemical activities in vivo (based on the properties and function of the transferred energy signature) is provided.

Applicant has thus specifically found that (i) when the biochemical scaffolds of the invention comprise a glycerol-based water solution and defined quantities of epimedium, stinging nettle, eleuthero root, damiana, *schisandra chinensis* berry, maca root, red Korean *ginseng*, ashwagandha, yohimbe, lion's mane mushroom (*hericium erinaceus*), vitamin $B_1$, vitamin $B_2$, vitamin $B_3$, vitamin $B_5$, vitamin $B_6$, vitamin $B_7$, vitamin $B_9$, vitamin $B_{12}$, vitamin E and cannabidiol (CBD) or waterhyssop (*bacopa monnieri*), ginger root, gotu kola (*centella asiatica*), huperzine A, lion's mane mushroom (*hericium erinaceus*), vitamin $B_1$, vitamin $B_2$, vitamin $B_3$, vitamin $B_5$, vitamin $B_6$, vitamin $B_7$, vitamin $B_9$, vitamin $B_{12}$, vitamin E, phosphatidylserine and CBD, (ii) are subjected to harmonic oscillation for a predetermined period of time and thereafter delivered to a subject, and (iii) delivered to a subject, the biochemical scaffolds induce enhanced seminal molecular and cell activity and, thereby, enhanced mental function and acuity of the subject, and thus also abate cognitive degradation associated with neurodegenerative diseases and disorders, if presented by the subject.

According to the invention, the diseases and disorders associated with cognitive degradation can comprise any disease or disorder, such as Alzheimer's Disease, vascular dementia, Lewy body dementia, Parkinson's disease, frontotemporal dementia, Creutzfeldt-Jakob disease, Wernicke-Korsakoff syndrome, mixed dementia, normal pressure hydrocephalus and Huntington's disease.

According to the invention, the biochemical scaffolds, i.e., liquid compositions thereof, can be subjected to various harmonic oscillations to achieve the above referenced enhanced seminal molecular and cell activity and, thereby, mental function and acuity.

Thus, in some embodiments, the harmonic oscillation comprises a frequency in the range of approximately 0.02 kHz to 10.5 kHz for a period of time in the range of at least 3.0 minutes to 60.0 minutes.

In some embodiments, the harmonic oscillation comprises sequential harmonic oscillation comprising a first frequency in the range of 0.9 kHz to 1.5 kHz for a first period of time in the range of 3.0 minutes to 60.0 minutes, and a second frequency in the range of 9.5 kHz to 10.5 kHz for a second period of time in the range of 3.0 minutes to 60.0 minutes.

In some embodiments, the harmonic oscillation comprises sequential harmonic oscillation comprising a first frequency in the range of 0.9 kHz to 1.5 kHz for a first period of time in the range of 3.0 minutes to 60.0 minutes, a second frequency in the range of 9.5 kHz to 10.5 kHz for a second period of time in the range of 3.0 minutes to 60.0 minutes, a third frequency in the range of 9.5 kHz to 11.0 kHz for a third period of time in the range of 3.0 minutes to 60.0 minutes, a fourth frequency in the range of 0.01 kHz to 0.03 kHz for a fourth period of time in the range of 3.0 minutes to 60.0 minutes, and a fifth frequency in the range of 0.004 kHz to 0.010 kHz for a fifth period of time in the range of 3.0 minutes to 60.0 minutes.

Applicant has further found that when a glycerol water solution, such as glycerol water solution 104 illustrated in FIG. 5, further comprises structured water, i.e., a glycerol structured water solution, and when at least one herb of the invention and the glycerol structured water solution are subjected to sequential harmonic oscillation at frequencies in the range of approximately 0.9-1.5 kHz, 9.5-10.5 kHz, 9.5-11.0 kHz, 0.01-0.03 kHz, and 0.004-0.010 kHz for a time period in the range of 3-60 minutes per frequency range, the water molecules in the glycerol structured water solution exhibit enhanced quantum coherence and, thus, form an enhanced plurality of energetic blanks comprising retained energy signatures of the herb.

Applicant has additionally found that when the glycerol structured water solution referenced above is delivered to and, hence, in communication with biological tissue the glycerol structured water solution, i.e., biochemical scaffold, induces enhanced biochemical activity via the resonant transfer of the retained energy signatures to the biological tissue and, hence, endogenous cells thereof.

Bioenergetic Platform

In some embodiments of the invention, the bioenergetic platforms of the invention comprise at least one Krebs cycle modulator, at least one glutathione modulator, at least one neurotransmitter modulator, at least one DNA modulator, at least one endocannabinoid system modulator, or at least one nuclear hormone receptor modulator.

In some embodiments of the invention, the bioenergetic platforms comprise at least one Krebs cycle modulator, at least one glutathione modulator, at least one neurotransmitter modulator, at least one DNA modulator, at least one endocannabinoid system modulator, and at least one nuclear hormone receptor modulator.

As indicated above, in one embodiment of the invention, the bioenergetic platforms comprise a plurality of Krebs cycle modulators, a plurality of neurotransmitter modulators, a glutathione modulator, a DNA modulator and an endocannabinoid system modulator.

As discussed in detail below, according to the invention, the Krebs cycle modulators, glutathione modulators, neurotransmitter modulators, DNA modulators, endocannabinoid system modulators, and nuclear hormone receptor modulators of the invention, alone and, particularly, in combination, when delivered to a subject, induce seminal molecular and cell activity, which (i) enhance mental function and acuity and (ii) abate cognitive degradation associated with neurodegenerative diseases and disorders, if presented.

Each of the noted modulators are discussed in detail below.

Krebs Cycle Modulators

As indicated above, the Krebs cycle modulators of the invention preferably comprise *schisandra chinensis* berry, epimedium, stinging nettle, yohimbe, red Korean *ginseng*, eleuthero root (or extract), damiana, ashwagandha, maca, L-arginine, L-citrulline, vitamin $B_1$, vitamin $B_2$, vitamin $B_3$, vitamin $B_5$, vitamin $B_7$, vitamin $B_9$, and vitamin $B_{12}$.

As also indicated above, according to the invention, the Krebs cycle modulators of the invention induce and/or modulate at least one Krebs cycle metabolic reaction, process and/or pathway, including, without limitation, Krebs cycle product inhibition and/or substrate availability.

As discussed in detail below, by virtue of the induced Krebs cycle activity, the Krebs cycle modulators of the invention enhance mental function and acuity, and abate cognitive degradation, if presented.

As set forth in priority U.S. application Ser. Nos. 14/223, 392, 16/116,539, 17/732,639, and 17/961,836, a seminal process associated with the Krebs cycle is the catabolism of carbohydrates, fats, and proteins, which results in the production of a two carbon organic product, i.e., acetate in the form of acetyl-CoA. Acetyl-CoA and two equivalents of water ($H_2O$) are consumed during the Krebs cycle, producing two equivalents of carbon dioxide ($CO_2$) and one equivalent of HS-CoA.

In addition, one complete cycle of the Krebs cycle converts three equivalents of nicotinamide adenine dinucleotide ($NAD^+$) into three equivalents of reduced $NAD^+$ (NADH), one equivalent of ubiquinone (Q) into one equivalent of reduced ubiquinone ($QH_2$), and one equivalent each of guanosine diphosphate (GDP) and inorganic phosphate ($P_i$) into one equivalent of guanosine triphosphate (GTP). The NADH and $QH_2$ generated during the Krebs cycle are in turn used by the oxidative phosphorylation pathway to generate energy-rich adenosine triphosphate (ATP).

A primary source of acetyl-CoA is carbohydrates, which are broken down by glycolysis to produce pyruvate. Pyruvate is decarboxylated by the enzyme pyruvate dehydrogenase to generate acetyl-CoA.

Regulation of the Krebs cycle is largely dependent upon product inhibition and substrate availability. For example, NADH, a product of all dehydrogenases in the cycle (with the exception of succinate dehydrogenase) inhibits pyruvate dehydrogenase, isocitrate dehydrogenase, α-ketoglutarate dehydrogenase, and citrate synthase. Acetyl-CoA inhibits pyruvate dehydrogenase, while succinyl-CoA inhibits alpha-ketoglutarate dehydrogenase and citrate synthase.

In a preferred embodiment, the Krebs cycle modulators of the invention also upregulate seminal Krebs cycle components and, thereby, induce enhanced seminal molecular and cell activity, support immune function and, hence, (i) enhance mental function and acuity and (ii) abate cognitive degradation associated with neurodegenerative diseases and disorders, if presented.

As discussed in detail herein, Krebs cycle converts three equivalents of nicotinamide adenine dinucleotide (NAD+) into three equivalents of reduced NAD+(NADH), which is an essential metabolite that is known to induce anti-inflammatory and antioxidant activity in brain tissue that is often associated with cognitive degradation due to inflammation-mediated neurodegenerative diseases and disorders, and support genomic stability, mitochondrial homeostasis, adaptive stress responses, and cell survival.

NAD+ is also a substrate for different NAD+ consuming proteins, which catabolize NAD+ to NAM. A seminal class of NAD+ consuming protein includes class III histone deacetylases sirtuins (SIRTs), which are upregulated in the presence of higher concentrations of NAD+ and regulate seminal cellular pathways, including pathways associated with neuronal survival and, hence, enhance mental function and acuity and abate neurodegenerative diseases and disorders presenting with cognitive degradation.

SIRTs are NAD+ dependent enzymes that regulate a wide spectrum of cellular pathways involved in neurodegenerative diseases and disorders presenting with cognitive degradation. By way of example, a seminal SIRT, i.e., SIRT1, promotes neurite outgrowth and associated axon development, in addition to regulating dendritic arborization, i.e., fine branching at distal ends of a nerve fibers, long-term potentiation and, thereby, enhances mental function and acuity by supporting learning and memory capabilities.

SIRT1 is also neuroprotective and, thus, protects neurons and, hence, brain tissue from neurodegenerative diseases and disorders presenting with cognitive degradation by interfering with and/or inhibiting cell signaling pathways responsible for the generation of amyloid precursor protein (APP). By virtue of interfering with and/or inhibiting cell signaling pathways responsible for the generation of amyloid precursor protein (APP), SIRT1 significantly reduces generation of amyloid beta peptide (Aβ) and, thereby, formation of amyloid plaques i.e., neurofibrillary tangles of Aβ peptide fibrils in the brain, which are often observed in neurodegenerative diseases and disorders that present with cognitive degradation and, hence, impaired mental function and acuity.

Further, SIRT1 directly deacetylates histone residue H3K9 of the p53 promoter, which results in reduced expression of the p53 gene and, thereby, promotes cell survival signaling pathways, hence, and protects healthy neurons from p53-mediated programmed cell death associated with neurotoxic cascades that cause deleterious cytoskeletal changes and neuronal dysfunction in a plurality of neurodegenerative diseases and disorders.

SIRT1 also retains the integrity of brain tissue; more particularly, white matter of the brain, which is often compromised by lesions in individuals afflicted with neurodegenerative diseases and/or disorders that present with a degradation in mental function and acuity. SIRT1 retains, and often restores, the integrity of white matter by inducing increased regenerative glial progenitor cell activity, e.g., differentiation, and, thereby, promoting white matter regeneration, which ameliorates the neurodegenerative diseases and/or disorders that present (or are associated) with degradation of mental function and acuity.

As indicated above, the Krebs cycle modulators of the invention are also capable of inducing and/or modulating product and/or substrate availability.

By way of example, Applicant has found that eleuthero root facilitates the formation of glucose-6-phosphate, which, as indicated above, converts to pyruvate, which enters the Krebs cycle as Acetyl-CoA and, thereby, facilitates conversion of NAD+ into reduced NAD+(NADH). The conversion of NAD+ into reduced NAD+(NADH) and, hence, the provision of an optimal NAD+/NADH ratio induces anti-inflammatory and antioxidant activity in brain tissue that is often associated with cognitive degradation due to inflammation-mediated neurodegenerative diseases and disorders. The noted conversion also supports genomic stability, mitochondrial homeostasis, adaptive stress responses, and cell survival.

As set forth in priority U.S. application Ser. Nos. 14/223,392 and 16/116,539, Applicant has also found that maca root works synergistically with eleuthero root by inducing co-factor proliferation, including the co-factor NAD+, which supports activation of the Krebs cycle and, thereby, numerous cell signaling pathways that are associated with enhancement of mental function and acuity.

Maca root also facilitates the production of super oxide dismutase, i.e., an important antioxidant. Intracellular super oxide dismutase converts a highly undesirable reactive oxygen species (ROS) known as superoxide to hydrogen peroxide and oxygen and, thereby, abates oxidative stress generated by superoxide in the brain that is associated with the injury and death of neurons during the progression of neurodegenerative diseases that present with cognitive degeneration, e.g., Parkinson's disease, Alzheimer's disease and amyotrophic lateral sclerosis (ALS).

As is well established, vitamin $B_1$, i.e., thiamine, is involved in RNA and DNA production, as well as nerve and mental function. Vitamin $B_1$'s active form is a coenzyme called thiamine pyrophosphate (TPP), which converts pyruvate to acetyl Coenzyme A (CoA). Vitamin $B_1$ is also a neuroprotective, site-directed antioxidant that neutralizes ROS proximate to neurons and, hence, protects the neurons from oxidative damage that is often observed in numerous neurodegenerative diseases and disorders that present with cognitive degradation and, hence, impaired mental function and acuity.

Vitamin $B_2$, i.e., riboflavin, is involved in energy production for the electron transport chain and catabolism of fatty acids, i.e., beta oxidation. Vitamin $B_2$ also ameliorates oxidative stress, mitochondrial dysfunction, neuroinflammation, and glutamate excitotoxicity often observed in numerous neurodegenerative diseases and disorders that present with cognitive degradation and, hence, impaired mental function and acuity.

Vitamin $B_3$, i.e., niacin, is composed of two co-enzyme forms of niacin: nicotinamide adenine dinucleotide (NAD), i.e., an NAD+ precursor, and nicotinamide adenine dinucleotide phosphate (NADP). As indicated above, the co-factor NAD+ induces anti-inflammatory and antioxidant activity in brain tissue that is often associated with cognitive degradation due to inflammation-mediated neurodegenerative diseases and disorders.

Vitamin $B_3$ also increases the ratio of NAD+/NADH in brain tissue and, thereby, also reduces DNA damage, neuroinflammation, and apoptosis of hippocampal neurons associated with a reduced NAD+/NADH ratio, which is often observed in neurodegenerative diseases and disorders that present with cognitive degradation and, hence, impaired mental function and acuity.

The increased ratio of NAD+/NADH in brain tissue also upregulates activity of neuroprotective SIRTs, e.g., SIRT3.

Vitamin $B_3$ thus enhances mental function and acuity by ameliorating defects in brain-energy metabolism and oxidative stress associated therewith, which are also often observed in neurodegenerative diseases and disorders that present with cognitive degradation and, hence, impaired mental function and acuity.

Vitamins $B_5$, $B_7$ and $B_9$ also enhance mental function and abate cognitive degradation by inducing and/or supporting seminal neurometabolic activities.

Vitamin $B_5$, i.e., pantothenic acid, is involved in the oxidation of fatty acids and carbohydrates. Coenzyme A, which can be synthesized from Vitamin $B_5$, is involved in the synthesis of several biological elements, including amino acids, phospholipids and most importantly, neurotransmitters, such as acetylcholine (ACh), which, as discussed in detail below, enhances mental function and acuity, and abates cognitive degradation.

Vitamin $B_7$, i.e., biotin, also plays a key role in the metabolism of lipids, proteins, and carbohydrates. Vitamin $B_7$ is a critical co-enzyme of four carboxylases: (i) acetyl CoA carboxylase, which is involved in the synthesis of fatty acids from acetate; (ii) propionyl CoA carboxylase, which is involved in gluconeogenesis; (iii) β-methylcrotonyl CoA carboxylase, which is involved in the metabolism of leucin; and (iv) pyruvate CoA carboxylase, which is involved in the metabolism of energy, amino acids, and cholesterol.

Vitamin $B_7$ also regulates and maintains optimal concentrations of glutamate, glutamine and dopamine, and optimal protein kinase A (PKA) activity in the hippocampus of the brain and, thereby, enhances mental function and acuity.

Vitamin $B_9$, i.e., folate or folic acid, acts as a co-enzyme in the form of tetrahydrofolate (THF), which is involved in the transfer of single-carbon units in the metabolism of nucleic acids and amino acids. THF is involved in pyrimidine nucleotide synthesis, which is required for normal cell division. Folate also aids in erythropoiesis, i.e., the production of red blood cells.

Further, Vitamin $B_9$ is a critical co-enzyme required for nucleotide synthesis in the hippocampus of the brain, which is one of the unique regions in the brain where cell renewal and DNA replication occurs. Folate thus enhances mental function and acuity by facilitating cell renewal and DNA replication in the hippocampus of the brain.

Vitamin $B_{12}$, i.e., cobalamin, is a coordination complex of cobalt, which occupies the center of a corrin ligand and is further bound to a benzimidazole ligand and adenosyl group. Vitamin $B_{12}$ induces and/or supports Krebs cycle activity by binding to methylmalonyl—coenzyme A (CoA) mutase and, thereby, mediates the isomerization of methylmalonyl CoA to succinyl CoA.

Vitamin $B_{12}$ also supports nervous system function and, thereby, enhances mental function and acuity by facilitating myelinogenesis, i.e., the formation and development of myelin sheath structures, which are critical structures of neurons that insulate the axon of neurons and enable consistent transmission of neurological signals through the axon.

Glutathione Modulators

According to the invention, the glutathione modulators of the invention enhance mental function and acuity, and abate cognitive degradation, if presented, by inducing several seminal neurometabolic and antioxidant activities.

As indicated above, the glutathione modulators of the invention also comprise one of the aforementioned herbs, i.e., *schisandra chinensis* berry, epimedium, stinging nettle, yohimbe, red Korean *ginseng*, eleuthero root (or extract), damiana, ashwagandha, maca root, iron (Fe), copper (Cu), and vitamins $B_1$, $B_2$, $B_3$, $B_5$, $B_7$, $B_9$ and $B_{12}$.

As also indicated above, the glutathione modulators of the invention induce (i) the generation or proliferation of glutathione and/or the glutathione family, including, without limitation, glutathione peroxidase, and/or (ii) catalase synthesis.

As also set forth in priority U.S. application Ser. Nos. 14/223,392 and 16/116,539, glutathione; specifically, glutathione peroxidase, is a key intracellular antioxidant that induces conversion of reactive oxygen species (ROS), such as hydrogen peroxide, to $H_2O$ and $O_2$.

As is well established, oxidative stress generated by ROS in the brain is associated with the injury and death of neurons during the progression of neurodegenerative diseases, e.g., Parkinson's disease, Alzheimer's disease and amyotrophic lateral sclerosis (ALS).

Glutathione reacts directly with ROS in nonenzymatic reactions to lower concentrations of ROS in the brain and, thereby, enhance mental function and acuity and abate cognitive degradation associated with neurodegenerative diseases and disorders, if presented.

Glutathione also lowers concentrations of ROS in the brain by serving as an electron donor for the reduction of peroxides in the glutathione peroxidase reaction. In the glutathione peroxidase reaction process, glutathione is converted to its oxidized form, i.e., glutathione disulfide (GSSG), which is also referred to as L-(−)-glutathione. After glutathione is converted to GSSG, the GSSG is reduced back to glutathione by glutathione reductase using reduced nicotinamide adenine dinucleotide phosphate (NADPH) as an electron donor and, hence, regenerates glutathione by transferring electrons from NADPH to GSSG, thus, forming a positive feedback loop that is adapted to continuously remove clinically deleterious ROS from the brain and, thereby, enhance mental function and acuity and abate cognitive degradation associated with neurodegenerative diseases and disorders, if presented.

As additionally set forth in priority U.S. application Ser. Nos. 14/223,392 and 16/116,539, vitamin $B_6$, i.e., pyridoxine, is stored in the body as pyridoxal 5'-phosphate (PLP), which is the co-enzyme form of vitamin $B_6$. Pyridoxine is also involved in the metabolism of amino acids and lipids; in the synthesis of key neurotransmitters, including gamma-aminobutyric acid (GABA) and serotonin, and hemoglobin, as well as in the production of nicotinic acid (vitamin $B_3$). Pyridoxine also plays an important role in gluconeogenesis.

Further, vitamin $B_6$ is also required for the synthesis of sphingolipids, which are critical components required to conduct myelinogenesis, i.e., the formation and development of myelin sheath structures, which, as discussed herein, are critical structures of neurons that insulate the axon of neurons and enable consistent transmission of neurological signals through the axon, and thereby, enhance mental function and acuity.

Neurotransmitter Modulators

Figure 3:
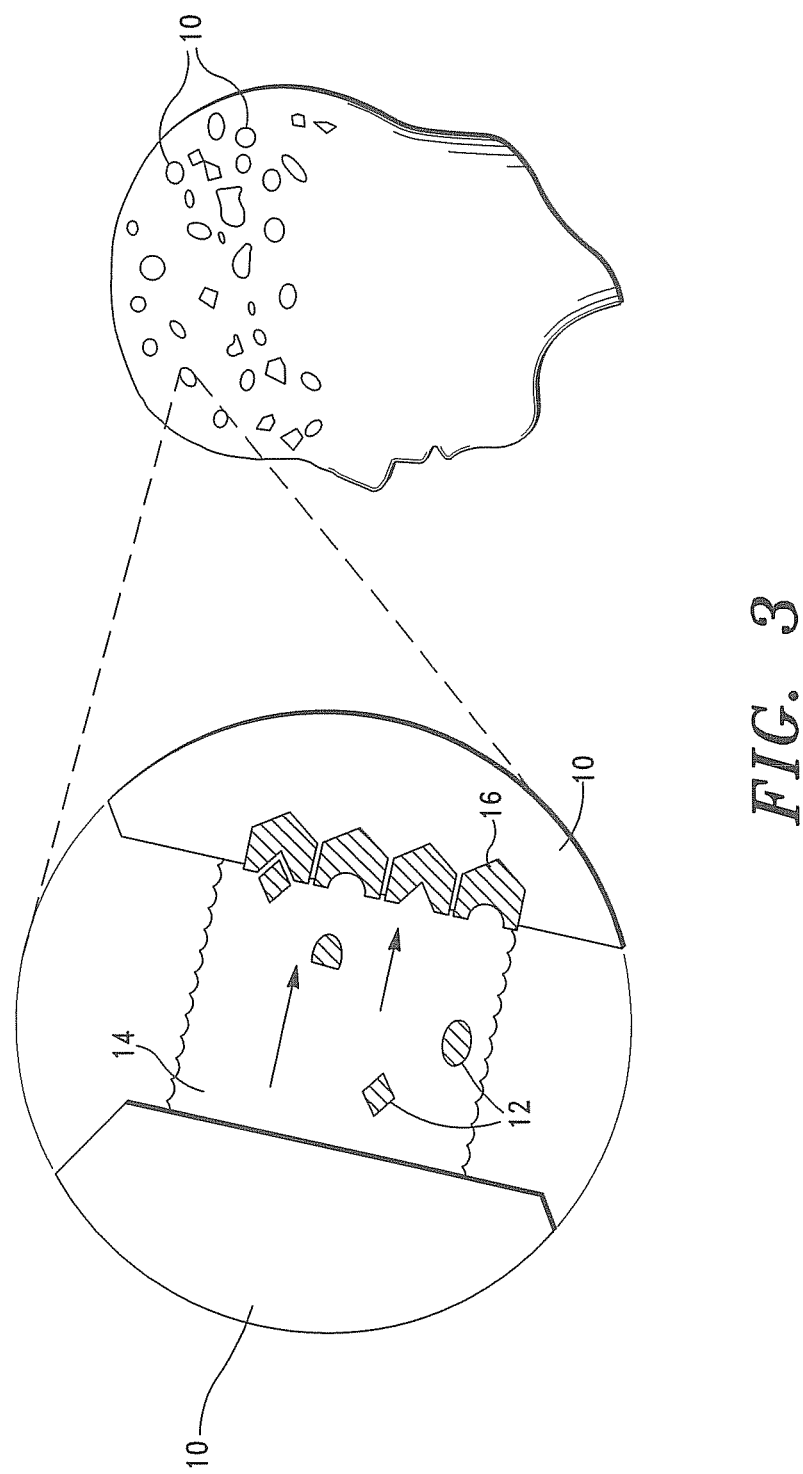
FIG. 3 is a schematic illustration of electrochemical signal transmission.

It is well established that the human brain contains large numbers of highly specialized cells called neurons. As illustrated in FIG. 3, the neurons 10 connect to and communicate with other neurons and, hence, cells via neurotransmitters 12, i.e., endogenous electrochemical signals, over synapses 14.

As further illustrated in FIG. 3 and discussed in detail below, when a sender neuron 10 generates and transmits neurotransmitters 12, the neurotransmitters 12 activate target receptors 16 on the receiver neuron 10 and, hence, initiate at least one seminal biological activity conducted by receiver neuron 10.

As indicated above, the neurotransmitter modulators of the invention preferably comprise epimedium, stinging nettle, maca root, eleuthero root, ginger root, Yohimbe, vitamin $B_1$, vitamin $B_6$, lion's mane mushroom (*hericium erinaceus*), waterhyssop (*bacopa monnieri*), gotu kola (*centella asiatica*), huperzine A, vitamin E and phosphatidylserine.

As also indicated above, according to the invention, the neurotransmitter modulators of the invention induce (and/or modulate) the generation or proliferation of at least one neurotransmitter, including acetylcholine (ACh), dopamine and norepinephrine, and/or the transmission thereof by and between neurons.

According to the invention, the neurotransmitter modulators of the invention similarly enhance mental function and acuity, and abate cognitive degradation, if presented, by inducing several seminal neurometabolic activities.

As set forth in priority U.S. application Ser. Nos. 14/223,392 and 16/116,539, ACh is a key neurotransmitter that stimulates the central nervous system to enhance mental acuity, i.e., learning ability, short term memory and mental focus.

Acetylcholine (ACh), dopamine and norepinephrine are also key neurotransmitters. ACh is functions as an inhibitory and excitatory neurotransmitter that modulates neuronal excitability, influences synaptic transmission, induces synaptic plasticity and coordinates the firing of groups of neurons. ACh also improves memory, motivation, and attention.

Dopamine similarly functions as an inhibitory and excitatory neurotransmitter. As inhibitory neurotransmitter, it causes balance and general sense of well-being. As excitatory neurotransmitter, it improves cognition, concentration and focus.

Norepinephrine also functions as an inhibitory and excitatory neurotransmitter that similarly improves cognition, as well as mood and mental concentration.

Phosphatidylserine, a seminal neurotransmitter modulator of the invention, induces the generation (or release) of ACh, dopamine and norepinephrine, and/or the transmission thereof by and between neurons.

Epimedium, yet another seminal neurotransmitter modulator of the invention, comprises the active element icariin, which lowers the amyloid precursor protein (APP) level and, hence, reduces amyloid beta peptide (Aβ) and, thereby, formation of amyloid plaques i.e., neurofibrillary tangles of AP peptide fibrils in the brain, which, as indicated above, are often observed in neurodegenerative diseases and disorders that present with cognitive degradation and, hence, impaired mental function and acuity.

As is well known, Tau proteins are used in the brain as axonal microtubule stabilizers. However, when the Tau proteins are hyperphosphorylated via glycogen synthase kinase-3 (GSK-3), amyloid beta proteins are generated, which can, and often will result in formation of amyloid plaques.

The hyperphosphorylation of Tau proteins is initiated in the locus coeruleus. Icariin abates hyperphosphorylation and, thus, reduces AP generation.

Icariin also facilitates the generation (or release) of ACh and, thereby, enhanced mental acuity by inhibiting acetylcholinesterase enzyme formation.

Applicant has also found that eleuthero root and lion's mane mushroom (*hericium erinaceus*) also stimulate the generation (or release) of ACh, which, as indicated above, enhances mental function and acuity.

Applicant has further found that (i) waterhyssop (*bacopa monnieri*) facilitates removal of formed amyloid beta plaques; (ii) that stinging nettle, ginger root, lion's mane mushroom (*hericium erinaceus*), and vitamin E reduce inflammation of brain tissue and, hence, brain cells, which is associated with impaired mental function; and (iii) that ginger root, waterhyssop (*bacopa monnieri*), gotu kola (*centella asiatica*), huperzine A and vitamin E also inhibit acetylcholinesterase enzyme formation and, hence, preserve ACh.

As set forth in priority U.S. application Ser. Nos. 14/223,392 and 16/116,539, Applicant has further found (i) stinging nettle increases the level of neurotransmitters available to act on the neuron receptors; particularly, the neurotransmitters dopamine and acetylcholine, thus improving several mental processes, e.g., learning and recollection abilities, (ii) in addition to inducing the Krebs cycle functions discussed above, eleuthero root also enhances neuron activities, e.g., short term memory, and (iii) Yohimbe also induces elevation of norepinephrine from the locus coeruleus, resulting in enhanced memory.

DNA Modulators

According to the invention, the DNA modulator(s) of the invention can comprise various biological or pharmacological agents.

As indicated above, the DNA modulators of the invention support and/or enhance mitochondrial DNA activity by, among other activities, protecting and/or facilitating the repair of mitochondrial DNA.

According to the invention, the DNA modulators of the invention enhance mental function and acuity, and abate cognitive degradation, if presented, by abating DNA damage and degradation and protecting and/or facilitating the repair of mitochondrial DNA to achieve optimal cell function and, thereby, physiological functioning.

As is well established and indicated above, mammalian mitochondria are organelles that produce more than 90% of cellular ATP. In addition to supplying ATP, i.e., cellular energy, mitochondria are also involved in other cellular mechanisms, including cellular differentiation, apoptosis, as well as cell cycle modulation and cell growth.

When a cell has temporarily or reversibly stopped dividing or regenerating it is often deemed to have entered a quiescent or senescent state referred to as the Go phase of the cell cycle.

Non-proliferative cells generally enter the senescent Go phase or state from the Gi phase and may remain senescent for long periods of time, possibly indefinitely (as is often the case for neurons). Senescence is very common for "adult" cells that are fully differentiated.

The maximum number of cell divisions that a cell can undergo, varies from cell type to cell type and organism. In fibroblasts, this number is about 50 divisions, after which cell division ceases.

However, some cells become senescent after fewer replication cycles as a result of DNA damage or degradation, e.g., DNA mutations, DNA oxidation, and chromosome losses, which would make a cell's progeny nonviable. If the DNA damage cannot be easily repaired, the cells either prematurely age or self-destruct (i.e., apoptosis or programmed cell death).

By way of example, individuals afflicted with a neurodegenerative disease or disorder, such as Alzheimer's disease, often have clinically significant populations of senescent neurons, which exhibit increased expression of cyclin-dependent kinase inhibitor 2D (CDKN2D/p19), in their brains caused in-part by DNA damage or degradation.

The process of cellular senescence can also be triggered by several additional mechanisms, including telomere shortening (i.e., a form of DNA damage or degradation).

Due to DNA replication mechanisms and oxidative stress, telomeres become progressively shorter with each round of replication. As increasing numbers of cell division occur, the telomeres reach a critically short length, which present as double-stranded DNA breaks, resulting in telomere-initiated senescence.

Protecting and/or facilitating the repair of mitochondrial DNA, which can be achieved by virtue of the DNA modulators of the invention, is thus essential to achieve optimal cell function and, thereby, physiological functioning. Healthy mitochondrial DNA also provides healthy enzymatic processes, which are required for oxidative phosphorylation and, hence, continued energy production.

As indicated above, a preferred DNA modulator comprises vitamin $B_{12}$.

According to the invention, $B_{12}$ supports DNA activity; specifically, DNA synthesis and, in most instances, enhances mental function and acuity and abates cognitive degradation associated with neurodegenerative diseases and disorders.

Vitamin $B_{12}$ also supports nervous system function and, thereby, enhances mental function and acuity by facilitating myelinogenesis, i.e., the formation and development of myelin sheath structures, which are critical structures of neurons that insulate the axon of neurons and enable consistent transmission of neurological signals through the axon.

Vitamin $B_{12}$ is also involved in the cellular metabolism of carbohydrates, proteins, and lipids. It functions as a co-enzyme in intermediary metabolism for the methionine synthase reaction with methylcobalamin, and the methylmalonyl CoA mutase reaction with adenosylcobalamin.

Endocannabinoid System Modulators

According to the invention, the endocannabinoid system modulators of the invention enhance mental function and acuity, and abate cognitive degradation, if presented, by modulating inflammation, i.e., reducing the neurochemical effects of beta-amyloid proteins and, thereby, reactive oxidative stress and reactive oxygen, and reducing adverse neuroinflammation.

As indicated above, the endocannabinoid system modulators of the invention induce cell receptor activity; preferably, cannabinoid receptor activity, i.e., receptors CB1 or CB2.

As also indicated above, a preferred endocannabinoid system modulator comprises cannabidiol (CBD).

CBD is one of many cannabinoid molecules produced by plants from the genus *cannabis*, second only to THC in abundance.

CBD activates the two seminal cannabinoid receptors (CB1 and CB2) and, hence, as discussed below, induces several significant physiological activities. One significant physiological activity induced by activating the CB1 and CB2 receptors is modulation of inflammatory activity of tissue and, hence cells, including brain tissue. The inflammation modulation, i.e., reduction thereof, is achieved by (among other factors) reducing the neurochemical effects of beta-amyloid proteins and, thereby, reactive oxidative stress and reactive oxygen.

As discussed below, in addition to activating the CB1 and CB2 receptors, CBD can, and in many instances will, enhance the levels of naturally-produced endocannabinoids, e.g., anandamide and 2-arachidonoyl glycerol (2-AG), by inhibiting the enzymes that break them down.

CBD also activates multiple serotonin receptors in the brain; particularly, serotonin 1A receptors. As a result, CBD can, and often will, abate cognitive degradation and enhance mental acuity.

Applicant has also found that CBD is also an effective neurotransmitter modulator. As indicated above, CBD activates the two seminal cannabinoid receptors CB1 and CB2. By activating the CB1 receptors, anandamide is increased and the associated elevation of corticosterone (stress hormone) and 2-arachidonoyl glycerol (2-AG) are reduced, which have a direct effect (and in many instances a calming effect) on the amygdala, i.e., the seminal emotional center of the brain.

Although CBD is a cannabinoid, CBD does not directly interact with and, hence, activate the CB1 and CB2 receptors. Instead, CBD indirectly activates the CB1 and CB2 receptors by modulating signaling through the CB1 and CB2 receptors by inhibiting the enzyme fatty acid amide hydrolase (FAAH). FAAH inactivates anandamide and also converts 2-AG to mono acylglycerol. By inhibiting FAAH more of anandamide and 2-AG available, which further enhances the calming effect on the amygdala.

In a preferred embodiment, the endocannabinoid system modulators(s) of the invention also upregulate seminal cannabinoid receptor activity and, thereby, induce enhanced seminal molecular and cell activity, and further modulate inflammation by reducing adverse neuroinflammation and, hence, enhances mental function and acuity.

CBD reduces adverse neuroinflammation by inducing (i) upregulation of the neuroprotective cytokines "interleukin-33" (IL-33) and "triggering receptor expressed on myeloid cells 2" (TREM2) expression in glial cells and (ii) down-regulating pro-inflammatory "interleukin-6" (IL-6) expression in peripheral blood leukocytes proximate to the glial cells. The upregulation of TREM2 expression induced in glial cells is also associated with reduced concentrations of amyloid precursor protein (APP) and, hence, amyloid beta peptide (Aβ) in the brain. The upregulation of IL-33 expression signals the recruitment of endogenous immune cells, such as microglia, to a biological insult site in the brain, thus, rapidly facilitating remodeling and regeneration of brain tissue and also abating glial scarring in the brain associated with cognitive degradation.

Nuclear Hormone Receptor Modulators

According to the invention, the nuclear hormone receptor modulators of the invention also enhance mental function and acuity, and abate cognitive degradation, if presented.

As indicated above, the nuclear hormone receptor modulators of the invention induce cell receptor activity; preferably, nuclear hormone receptor modulator activity, e.g., the activity of nuclear hormone receptor modulators estrogen receptor-α (ERα), estrogen receptor-(ERβ), androgen receptor (AR), and mineralocorticoid receptor (MR).

As also indicated above, a preferred nuclear hormone receptor modulator comprises red Korean *ginseng*. As is well established, red Korean *ginseng* comprises a plurality of ginsenosides, including, without limitation, ginsenoside Rb-1, ginsenoside Rg-1, ginsenoside Re, ginsenoside Rg3, ginsenoside Rg5, ginsenoside Rh2, ginsenoside Rh1, ginsenoside Rh3, ginsenoside Rh4, ginsenoside Rs3, ginsenoside Rb-2, ginsenoside Rd, ginsenoside Rp-1, and ginsenoside F4.

As is also well established, ginsenosides (also referred to as "panaxosides") are classified as both steroid glycosides and triterpene saponins. Ginsenosides are derived exclusively from plants belonging to the genus *panax* (i.e., *ginseng*), and exhibit a multitude of biological effects that mimic seminal biological activities of anti-inflammatory steroidal drugs that bind to and activate nuclear hormone receptors. Ginsenosides are thus lipophilic in nature, and by virtue of their steroidal backbone, they can traverse cell membranes of mammalian cells by simple diffusion and regulate cellular functions by binding to specific intracellular target proteins in the cytoplasm and nucleus of the mammalian cells.

It has also been found and Applicant has confirmed that ginsenosides activate seminal nuclear hormone receptors (e.g., ERα, ERβ, AR, and MR) and, hence, as discussed below, induce several significant physiological activities. One significant physiological activity induced by activating the nuclear hormone receptors is the modulation of inflammatory activity and diseases associated therewith, including neuroinflammatory activity associated with impaired mental acuity and memory.

The modulation of inflammatory activity, i.e., reduction thereof, is achieved by (among other factors) suppressing the production of seminal proinflammatory cytokines and, thereby modulating the activities of inflammatory signaling pathways, such as nuclear factor-κB (NF-κB) and activator protein-1 signaling pathways.

Ginsenoside Rb1 inhibits TNF-α production in macrophages and suppresses the activation of NF-κB, which is a key regulator of inflammatory activity, as well as a modulator of TNF-α production in macrophages. Ginsenoside Rb1 also significantly reduces activation of interleukin-1 (IL-1) receptor-associated kinase (IRAK-1), which is an inhibitor of κB (IκB) kinase (IKK)-α, NF-κB, and mitogen-activated protein kinases (MAPKs).

Ginsenosides also exhibit seminal neuroprotective effects by modulating, i.e., reducing neuroinflammatory activity in brain tissue and in the central nervous system (CNS), by, among other activities, regulating free radical scavenging pathways and reducing inflammatory responses in late-stage ischemia by the inhibiting the expression of inducible nitric oxide synthase (iNOS) and prostaglandin-endoperoxide synthase 2 (COX-2).

As is well established, lipopolysaccharide (LPS)-induced neuroinflammatory activity is associated with various neurodegenerative diseases, including Parkinson disease, Alzheimer's disease (AD), and multiple sclerosis. LPS compounds activate microglial cells in the brain and CNS that promote and induce neuroinflammatory activities associated with the noted neurodegenerative diseases.

Ginsenoside Re, in particular, reduces inflammatory activity in the brain and CNS by inhibiting proinflammatory mediators (i.e., iNOS and COX2) that are generated in response to mammalian cell exposure to LPS and inhibiting activation of the p38-MAPK signaling pathway in microglial cells.

Ginsenoside Rg1 similarly modulates microglial cell activation by reducing the production of tumor necrosis factor-α (TNF-α) and NO as well as the expression of iNOS and ionized calcium-binding adapter molecule 1 (Iba-1) by inhibiting the activation of NF-κB and MAPKs pathways.

It has also been found that ginsenoside Rg1 also facilitates protection of other biological tissues, e.g., hepatic tissue, from ischemia/reperfusion (IR) injury by reducing inflammatory activity and associated apoptosis events resulting therefrom by modulating NF-κB and ROS—NO—hypoxia-inducible factor signaling pathways.

IR injury; more particularly, IR injury of the brain and CNS is also ameliorated via Ginsenoside Rg1 mediated activation of peroxisome proliferator-activated receptor-γ/heme oxygenase-1 (HO-1), suppression of protease-activated receptor-1 expression, and inhibition of mitogen-activated protein kinase 14 (p38a MAPK), and, hence, inhibited activation of the p38-MAPK cell signaling pathway.

Thus, in some embodiments of the invention, the biochemical scaffolds of the invention comprise a liquid composition comprising a liquid medium and at least one of the aforementioned Krebs cycle modulators, neurotransmitter modulators, glutathione modulators, DNA modulators, endocannabinoid system modulators or nuclear hormone receptor modulators.

In some embodiments of the invention, the biochemical scaffolds of the invention comprise a liquid composition comprising a liquid medium and a Krebs cycle modulator, neurotransmitter modulator, glutathione modulator, DNA modulator, endocannabinoid system modulator and nuclear hormone receptor modulator.

As indicated above, in one preferred embodiment, the biochemical scaffolds of the invention comprise a liquid composition comprising a liquid medium, a plurality of Krebs cycle modulators, a plurality of neurotransmitter modulators, a glutathione modulator, a DNA modulator and an endocannabinoid system modulator.

In a preferred embodiment, the liquid medium comprises glycerin-based water.

In a preferred embodiment, the Krebs cycle modulators comprise vitamin $B_1$, vitamin $B_2$, vitamin $B_3$, vitamin $B_5$ and vitamin $B_9$.

In a preferred embodiment, the neurotransmitter modulators comprise ginger root, lion's mane mushroom (*hericium erinaceus*), waterhyssop (*bacopa monnieri*), gotu kola (*centella asiatica*), huperzine A, vitamin E, phosphatidylserine and vitamin $B_6$.

In a preferred embodiment, the glutathione modulator comprises vitamin $B_7$.

In a preferred embodiment, the DNA modulator comprises vitamin $B_{12}$.

In a preferred embodiment, the endocannabinoid system modulator comprises cannabidiol (CBD).

In a preferred embodiment, the liquid medium, i.e., glycerin-based water, comprises in the range of approximately 235 ml to 245 ml.

The preferred quantities of the biochemical scaffold components referenced above are set forth in Table I below.

TABLE I

| Biochemical Scaffold Component | Quantity |
| --- | --- |
| waterhyssop (*bacopa monnieri*) | approx. 330.0 mg to approx. 1000.0 mg |
| ginger root | approx. 500.0 mg to approx. 3000.0 mg |
| gotu kola (*centella asiatica*) | approx. 50.0 mg to approx. 1000.0 mg |
| lion's mane mushroom (*hericium erinaceus*) | approx. 250.0 mg to approx. 1000.0 mg |
| huperzine A | approx. 0.2 mg to approx. 0.5 mg |
| vitamin $B_1$ | approx. 5.0 mg to approx. 7.0 mg |
| vitamin $B_2$ | approx. 0.60 mg to approx. 0.80 mg |
| vitamin $B_3$ | approx. 8.0 mg to approx. 12.0 mg |
| vitamin $B_5$ | approx. 8.0 mg to approx. 12.0 mg |
| vitamin $B_6$ | approx. 1.0 mg to approx. 3.0 mg |
| vitamin $B_7$ | approx. 0.055 mg to approx. 0.065 mg |
| vitamin $B_9$ | approx. 0.155 mg to approx. 0.165 mg |
| vitamin $B_{12}$ | approx. 0.995 mg to approx. 1.005 mg |
| vitamin E | approx. 170.0 IU to approx. 190 IU |
| phosphatidylserine | approx. 250.0 mg to approx. 500.0 mg |
| cannabidiol (CBD) | approx. 12.0 mg to approx. 13.0 mg |

In another preferred embodiment of the invention, the Krebs cycle modulators comprise *schisandra chinensis* berry, stinging nettle, yohimbe, red Korean *ginseng*, eleuthero root (or extract), damiana, ashwagandha, maca root, vitamin $B_1$, vitamin $B_2$, vitamin $B_3$, vitamin $B_5$ and vitamin $B_9$.

In the noted preferred embodiment, the neurotransmitter modulators comprise epimedium, lion's mane mushroom (*hericium erinaceus*), vitamin E and vitamin $B_6$, the glutathione modulator similarly comprises vitamin $B_7$, the DNA modulator similarly comprises vitamin $B_{12}$ and the endocannabinoid system modulator similarly comprises cannabidiol (CBD).

The preferred quantities of the biochemical scaffold components referenced above are set forth in Table II below.

TABLE II

| Biochemical Scaffold Component | Quantity |
|---|---|
| epimedium | approx. 1175.0 mg to approx. 2350.0 mg |
| stinging nettle | approx. 1175.0 mg to approx. 2350.0 mg |
| yohimbe | approx. 1175.0 mg to approx. 2350.0 mg |
| red Korean ginseng | approx. 1175.0 mg to approx. 2350.0 mg |
| eleuthero root | approx. 1175.0 mg to approx. 2350.0 mg |
| damiana | approx. 1175.0 mg to approx. 2350.0 mg |
| schisandra chinensis berry | approx. 1175.0 mg to approx. 2350.0 mg |
| ashwagandha | approx. 1175.0 mg to approx. 2350.0 mg |
| maca root | approx. 1175.0 mg to approx. 2350.0 mg |
| lion's mane mushroom (hericium erinaceus) | approx. 250.0 mg to approx. 1000.0 mg |
| vitamin $B_1$ | approx. 5.0 mg to approx. 7.0 mg |
| vitamin $B_2$ | approx. 0.60 mg to approx. 0.80 mg |
| vitamin $B_3$ | approx. 8.0 mg to approx. 12.0 mg |
| vitamin $B_5$ | approx. 8.0 mg to approx. 12.0 mg |
| vitamin $B_6$ | approx. 1.0 mg to approx. 3.0 mg |
| vitamin $B_7$ | approx. 0.055 mg to approx. 0.065 mg |
| vitamin $B_9$ | approx. 0.155 mg to approx. 0.165 mg |
| vitamin $B_{12}$ | approx. 0.995 mg to approx. 1.005 mg |
| vitamin E | approx. 170.0 IU to approx. 190 IU |
| cannabidiol (CBD) | approx. 12.0 mg to approx. 13.0 mg |

As indicated above, in a preferred embodiment of the invention, the biochemical scaffolds of the invention are subjected to harmonic oscillation at a defined frequency or frequencies and a defined period of time or times.

In some embodiments, the harmonic oscillation comprises a frequency in the range of approximately 0.02 kHz to 10.5 kHz for a period of time in the range of at least 3.0 minutes to 60.0 minutes.

In some embodiments, the harmonic oscillation comprises sequential harmonic oscillation comprising a first frequency in the range of 0.9 kHz to 1.5 kHz for a first period of time in the range of 3.0 minutes to 60.0 minutes, and a second frequency in the range of 9.5 kHz to 10.5 kHz for a second period of time in the range of 3.0 minutes to 60.0 minutes.

In some embodiments, the harmonic oscillation comprises sequential harmonic oscillation comprising a first frequency in the range of 0.9 kHz to 1.5 kHz for a first period of time in the range of 3.0 minutes to 60.0 minutes, a second frequency in the range of 9.5 kHz to 10.5 kHz for a second period of time in the range of 3.0 minutes to 60.0 minutes, a third frequency in the range of 9.5 kHz to 11.0 kHz for a third period of time in the range of 3.0 minutes to 60.0 minutes, a fourth frequency in the range of 0.01 kHz to 0.03 kHz for a fourth period of time in the range of 3.0 minutes to 60.0 minutes, and a fifth frequency in the range of 0.004 kHz to 0.010 kHz for a fifth period of time in the range of 3.0 minutes to 60.0 minutes.

According to the invention, there are thus also provided methods for enhancing mental function and acuity of a subject. In one embodiment, the method comprises:
  (i) providing a biochemical scaffold comprising a liquid composition comprising glycerin-based water, water-hyssop (bacopa monnieri), lion's mane mushroom (hericium erinaceus), vitamin E and cannabidiol (CBD);
  (ii) subjecting the biochemical scaffold to harmonic oscillation; and
  (iii) delivering a therapeutically effective amount of the biochemical scaffold to the subject.

In some embodiments, the biochemical scaffold further comprises ginger root.

In some embodiments, the biochemical scaffold further comprises huperzine A.

In some embodiments, the biochemical scaffold further comprises phosphatidylserine.

In some embodiments, the biochemical scaffold further comprises vitamin $B_6$.

The preferred quantities of the aforementioned biochemical scaffold components set forth in Table II.

In some embodiments, the harmonic oscillation comprises a frequency in the range of approximately 0.02 kHz to 10.5 kHz for a period of time in the range of at least 3.0 minutes to 60.0 minutes.

In some embodiments, the harmonic oscillation comprises sequential harmonic oscillation comprising a first frequency in the range of 0.9 kHz to 1.5 kHz for a first period of time in the range of 3.0 minutes to 60.0 minutes, and a second frequency in the range of 9.5 kHz to 10.5 kHz for a second period of time in the range of 3.0 minutes to 60.0 minutes.

In some embodiments, the harmonic oscillation comprises sequential harmonic oscillation comprising a first frequency in the range of 0.9 kHz to 1.5 kHz for a first period of time in the range of 3.0 minutes to 60.0 minutes, a second frequency in the range of 9.5 kHz to 10.5 kHz for a second period of time in the range of 3.0 minutes to 60.0 minutes, a third frequency in the range of 9.5 kHz to 11.0 kHz for a third period of time in the range of 3.0 minutes to 60.0 minutes, a fourth frequency in the range of 0.01 kHz to 0.03 kHz for a fourth period of time in the range of 3.0 minutes to 60.0 minutes, and a fifth frequency in the range of 0.004 kHz to 0.010 kHz for a fifth period of time in the range of 3.0 minutes to 60.0 minutes.

As set forth in priority U.S. application Ser. No. 14/223,392, the biochemical scaffolds of the invention can be delivered to host tissue by various conventional means, including, without limitation, oral, sublingual, nasal, direct injection, topical application, etc.

As will readily be appreciated by one having ordinary skill in the art, the present invention provides numerous advantages compared to prior art formulations and methods for enhancing cell function and, thereby mental function and acuity. Among the advantages are the following:

The provision of biochemical scaffolds and methods associated therewith that enhance physical and mental function by inducing and/or modulating a plurality of seminal molecular and cell activities.

The provision of biochemical scaffolds and methods associated therewith that enhance mental function and acuity by inducing at least one Krebs cycle metabolic reaction, process and/or pathway.

The provision of biochemical scaffolds biochemical scaffolds and methods associated therewith that enhance mental function and acuity by inducing the enhanced generation of neurotransmitters and/or modulating the transmission thereof by and between neurons.

The provision of biochemical scaffolds biochemical scaffolds and methods associated therewith that enhance mental function and acuity by inducing cell receptor activity.

The provision of biochemical scaffolds biochemical scaffolds and methods associated therewith that enhance mental function and acuity by modulating the endocannabinoid system.

The provision of biochemical scaffolds biochemical scaffolds and methods associated therewith that enhance mental function and acuity by inducing and/or modulating mitochondria DNA activity.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method of enhancing mental function and acuity of a subject, comprising of the steps:
   forming a liquid composition comprising glycerin-based water, waterhyssop in the range of from about 330.0 mg to about 1000.0 mg, gotu kola in the range of from about 50.0 mg to about 1000.0 mg, lion's mane mushroom in the range of from about 250.0 mg to about 1000.0 mg,
   vitamin $B_1$ in the range of from about 5.0 mg to about 7.0 mg, vitamin E in the range of from about 170 IU to about 190 IU, and cannabidiol in the range of from about 12.0 mg to about 13.0 mg;
   subjecting said liquid composition to harmonic oscillation, said harmonic oscillation consisting of a frequency in the range of 0.02 kHz to 10.5 kHz for a period of time in the range of 3.0 minutes to 60.0 minutes; and
   delivering a therapeutically effective amount of said liquid composition to said subject.

2. The method of claim 1, wherein said liquid composition further comprises ginger root in the range of from about 500.0 mg to about 3000.0 mg.

3. The method of claim 1, wherein said liquid composition further comprises huperzine A in the range of from about 0.2 mg to about 0.5 mg.

4. The method of claim 1, wherein said liquid composition further comprises phosphatidylserine in the range of from about 250.0 mg to about 500.0 mg.

5. The method of claim 1, wherein said liquid composition further comprises vitamin $B_6$ in the range of 1.0 mg to 3.0 mg and vitamin $B_{12}$ in the range of 0.995 mg to 1.005 mg.

6. The method of claim 1, wherein said glycerin-based water comprises in the range from about 235.0 ml to about 245.0 ml.

7. A method of enhancing mental function and acuity of a subject, comprising of the steps:
   forming a liquid composition comprising glycerin-based water, waterhyssop in the range of from about 330.0 mg to about 1000.0 mg, gotu kola in the range of from about 50.0 mg to about 1000.0 mg, lion's mane mushroom in the range of from about 250.0 mg to about 1000.0 mg,
   vitamin $B_1$ in the range of from about 5.0 mg to about 7.0 mg, vitamin E in the range of from about 170 IU to about 190 IU, and cannabidiol in the range of from about 12.0 mg to about 13.0 mg;
   subjecting said liquid composition to sequential harmonic oscillation, said sequential harmonic oscillation consisting of a first frequency in the range of 0.9 kHz to 1.5 kHz for a first period of time in the range of 3.0 minutes to 60.0 minutes and a second frequency in the range of 9.5 kHz to 10.5 kHz for a second period of time in the range of 3.0 minutes to 60.0 minutes; and
   delivering a therapeutically effective amount of said liquid composition to said subject.

8. The method of claim 7, wherein said liquid composition further comprises vitamin $B_6$ in the range of 1.0 mg to 3.0 mg and vitamin $B_{12}$ in the range of mg to 1.005 mg.

9. The method of claim 8, wherein said sequential harmonic oscillation further comprises a third frequency in the range of 9.5 kHz to 11.0 kHz for a third period of time in the range of 3.0 minutes to 60.0 minutes, a fourth frequency in the range of kHz to 0.03 kHz for a fourth period of time in the range of 3.0 minutes to 60.0 minutes, and a fifth frequency in the range of 0.004 kHz to 0.010 kHz for a fifth period of time in the range of 3.0 minutes to 60.0 minutes.

10. A method of enhancing mental function and acuity of a subject, comprising of the steps:
    forming a liquid composition comprising glycerin-based water, waterhyssop in the range of from about 330.0 mg to about 1000.0 mg, ginger root in the range of from about 500.0 mg to about 3000.0 mg, gotu kola in the range of from about 50.0 mg to about 1000.0 mg, huperzine A in the range of from about 0.2 mg to about 0.5 mg, lion's mane mushroom in the range of from about 250.0 mg to about 1000.0 mg,
    vitamin $B_1$ in the range of from about 5.0 mg to about 7.0 mg, vitamin $B_2$ in the range of from about 0.60 mg to about 0.80 mg, vitamin $B_3$ in the range of from about 8.0 mg to about 12.0 mg, vitamin $B_5$ in the range of from about 8.0 mg to about 12.0 mg, vitamin $B_6$ in the range of from about 1.0 mg to about 3.0 mg, vitamin $B_7$ in the range of from about 0.055 mg to about mg, vitamin $B_9$ in the range of from about 0.155 mg to about 0.165 mg, vitamin $B_{12}$ in the range of from about 0.995 mg to about 1.005 mg, vitamin E in the range of from about 170 IU to about 190 IU,
    phosphatidylserine in the range of from about 250.0 mg to about 500.0 mg, and
    cannabidiol in the range of from about 12.0 mg to about 13.0 mg;
    subjecting said liquid composition to sequential harmonic oscillation, said sequential harmonic oscillation consisting of a first frequency in the range of 0.9 kHz to 1.5 kHz for a first period of time in the range of 3.0 minutes to 60.0 minutes, a second frequency in the range of 9.5 kHz to 10.5 kHz for a second period of time in the range of 3.0 minutes to 60.0 minutes, a third frequency in the range of 9.5 kHz to 11.0 kHz for a third period of time in the range of 3.0 minutes to 60.0 minutes, a fourth frequency in the range of 0.01 kHz to 0.03 kHz for a fourth period of time in the range of 3.0 minutes to 60.0 minutes, and a fifth frequency in the range of kHz to 0.010 kHz for a fifth period of time in the range of 3.0 minutes to 60.0 minutes; and
    delivering a therapeutically effective amount of said liquid composition to said subject.

* * * * *